(12) United States Patent
Hose

(10) Patent No.: US 9,410,879 B1
(45) Date of Patent: Aug. 9, 2016

(54) HIGH DEFINITION BLOOD TRAILING FLASHLIGHT

(71) Applicant: Primos, Inc., Flora, MS (US)

(72) Inventor: Mark D. Hose, Huntsville, AL (US)

(73) Assignee: PRIMOS, INC., Flora, MS (US)

( * ) Notice: Subject to any disclaimer, the term of this patent is extended or adjusted under 35 U.S.C. 154(b) by 84 days.

(21) Appl. No.: 14/262,469

(22) Filed: Apr. 25, 2014

(51) Int. Cl.
*F21V 9/00* (2015.01)
*G01N 21/29* (2006.01)
*F21K 99/00* (2016.01)
*F21L 4/02* (2006.01)

(52) U.S. Cl.
CPC ........ *G01N 21/29* (2013.01); *F21K 9/56* (2013.01); *F21L 4/027* (2013.01); *F21V 9/00* (2013.01)

(58) Field of Classification Search
CPC ............. F21K 9/56; F21L 4/027; F21V 9/00; F21V 9/083; G01N 21/29
USPC ............................. 362/166–170, 293, 311.02
See application file for complete search history.

(56) References Cited

U.S. PATENT DOCUMENTS

| | | | |
|---|---|---|---|
| 1,613,203 A | 1/1927 | Shannon | |
| 1,946,059 A | 2/1934 | Buchholz | |
| 4,725,460 A | 2/1988 | Matsuo et al. | |
| 4,804,850 A | 2/1989 | Norrish et al. | |
| 4,963,798 A | 10/1990 | McDermott | |
| 5,363,152 A | 11/1994 | Reed, III | |
| 5,909,062 A * | 6/1999 | Krietzman | H02J 9/061 307/150 |
| 6,250,771 B1 | 6/2001 | Sharrah et al. | |
| 6,290,368 B1 | 9/2001 | Lehrer | |
| 6,334,680 B1 | 1/2002 | Larson | |
| 6,485,160 B1 | 11/2002 | Sommers et al. | |
| 6,862,093 B2 | 3/2005 | Peng et al. | |
| 7,040,780 B2 | 5/2006 | Diehl | |
| 7,066,622 B2 | 6/2006 | Alessio | |
| 7,172,312 B2 | 2/2007 | Chen | |
| 7,290,896 B2 | 11/2007 | Dallas et al. | |
| 7,621,653 B2 | 11/2009 | Hendrie | |
| 7,682,037 B1 | 3/2010 | Hose et al. | |
| 7,699,482 B2 | 4/2010 | Noguchi | |
| 7,988,318 B1 | 8/2011 | Smith et al. | |
| 2003/0227774 A1 | 12/2003 | Martin et al. | |
| 2004/0200980 A1 | 10/2004 | Blackwell et al. | |
| 2004/0223342 A1 | 11/2004 | Klipstein et al. | |
| 2007/0086186 A1 | 4/2007 | Rohlfing et al. | |
| 2007/0195420 A1 | 8/2007 | Fitchmun | |
| 2008/0158875 A1 | 7/2008 | Kim et al. | |

OTHER PUBLICATIONS

Coolflashlights.com. "Hunting LED flashlights", archived Feb. 20, 2006, available http://web.archive.org/web/2006022015119/http:///www.coolflashlights.com/hunting_lights.html (3 of 3) Jul. 21, 2008 3:42:12 PM.
Advertisement on Ebay for Winchester Blood Trail Tracking L.E.D. Flashlight; Apr. 18, 2007.

* cited by examiner

*Primary Examiner* — Jason Moon Han
(74) *Attorney, Agent, or Firm* — Holland & Hart

(57) ABSTRACT

A light-emitting device configured to illuminate blood includes a white light source configured to emit white light, and a filter configured to progressively attenuate portions of the white light having wavelengths up to a transition wavelength within a red light spectrum of the white light. The transition wavelength may be in the range of about 610 nm to about 618 nm.

26 Claims, 10 Drawing Sheets

HIGH DEFINITION BLOOD TRAILING FLASHLIGHT

BACKGROUND

Hunters often try to track wounded game by following a blood trail. Law enforcement officers and military personnel may also need to track a trail of blood. Following a blood trail at night may be challenging because blood is often difficult to identify at night, even if the tracker is using a high-powered flashlight. One problem with traditional flashlights is that they may flood a user's eye with a broad spectrum of light, making it difficult for the user to distinguish between the color(s) of blood and other colors.

Traditional light sources have limited effectiveness as they are not optimized to the optical properties of blood or to the response of the human vision system. Traditional light sources used today to locate blood utilize a variety of elements such as bulbs (incandescent, xenon, or halogen), light emitting diodes (white LEDs), and burning gases (lanterns). These lights are not optimized to the reflective properties of blood or to the visual response of the human eye. Incandescent bulbs produce a yellow cast (yellowish/white). Many of the white LEDs available today have a blue cast (bluish/white). Many high intensity white light sources tend to saturate the human eye.

Application specific light sources may be optimized to the optical properties of blood and to the related response of the human vision system. However, these devices use combinations of colored light sources (e.g., additive methods) that produce colored interference shadows, which may create significant distraction when tracking blood in brush and tall grass. Application specific lights utilize an additive method whereby combinations of lighting elements (e.g., green and red LEDs, or blue and red LEDS). While these combinations produce output spectrums that enhance the detection of blood, they may have the drawback of producing colored interference shadows. In an outdoor environment, colored shadows appear on the ground when tracking blood in tall grass or brush. These devices cast the obvious dark shadows on the ground when shining through the brush. These shadows are also outlined with thin colored boarders (e.g., green and red, or blue and red), which may be distractions to the user.

SUMMARY

One aspect of the present disclosure relates to a light-emitting device configured to illuminate blood. The light-emitting device includes a white light source configured to emit white light, and a filter configured to progressively attenuate portions of the white light having wavelengths up to a transition wavelength that exists within a red light spectrum of the white light.

The transition wavelength is optimally about 614 nm. The transition wavelength may be in the range of about 610 nm to about 618 nm. Portions of the white light closest to and below the transition wavelength may be the most attenuated by the filter. Portions of the white light at or above the transition wavelength may be unattenuated. Yellow portions of the white light may be partially attenuated, orange portions of the white light may be more attenuated than the yellow portions, and red portions of the white light having a non-blood red color may be more attenuated than the orange portions. The filter may be adjustable between an operable position in which the white light is filtered, and an inoperable position in which the white light is not filtered. The light-emitting device may further include at least one of an optical lens and a reflector positioned between the white light source and the filter.

Another aspect of the present disclosure relates to a light-emitting device configured to illuminate blood. The light-emitting device includes a flashlight housing, a white light source mounted to the flashlight housing and configured to emit white light, a filter mounted to the flashlight housing, and at least one of an optical lens and a reflector mounted to the flashlight housing between the white light source and the filter. The filter progressively attenuates portions of the white light up to a wavelength of no greater than about 618 nm.

The filter may pass all portions of the white light having wavelengths greater than about 618 nm. The filter may attenuate portions of the white light having wavelengths up to a wavelength in the range of about 610 nm to about 618 nm. The filter may attenuate all portions of the white light less than about 618 nm. The filter may attenuate non-blood red color portions of the white light having wavelengths less than about 618 nm to a greater extent than the attenuation of the yellow and orange portions of the white light. The filter may attenuate portions of the white light between an upper critical wavelength and a lower critical wavelength.

The upper critical wavelength may be in the range of about 610 nm to about 618 nm, and the lower critical wavelength may be in the range of about 550 nm and about 570 nm. The filter may include glass mixed with at least one rare earth mineral, or include amethyst contrast enhancement (ACE) glass. The at least one rare earth mineral of the filter may include Didymium. The filter may include interference patterns applied to at least one of glass, quartz and plastic. The filter and the optical lens may be formed as a single, monolithic structure.

A further aspect of the present disclosure relates to a method of illuminating blood. The method includes providing a light-emitting device having a white light source and a filter, generating white light with the white light source, attenuating with the filter portions of the white light having wavelengths up to a range of about 610 nm to about 618 to form a filtered light beam, and emitting the filtered light beam from the light-emitting device to illuminate a target location, causing a blood red color in the target location to be perceived as standing out in contrast to non-blood red colors.

Attenuating with the filter portions of the white light may include attenuating all portions of the white light up to and including non-blood red colors having a wavelength less than the range of about 610 nm to about 618 nm. Attenuating with the filter portions of the white light may include passing all portions of the white light having wavelengths greater than the range of about 610 nm to about 618 nm. Attenuating with the filter portions of the white light may include progressively attenuating lower wavelength portions of the white light approaching the range of about 610 nm to about 618 nm. Attenuating portions of the white light includes progressively attenuating wavelengths from about 550 nm up to about 610 nm.

Another aspect of the present disclosure relates to a light-emitting device configured to illuminate blood. The light-emitting device includes a flashlight housing, at least one light source mounted to the flashlight housing and configured to emit a plurality of different colors using a plurality of different light modes, a filter mounted to the flashlight housing, and a reflector mounted to the flashlight housing between the at least one light source and the filter. The filter progressively attenuates portions of the light in at least some light modes up to a wavelength in the range of about 610 nm to about 618 nm.

The filter may pass all portions of the light having wavelengths greater than about 618 nm. The at least one light source may include a plurality of multi-color LEDs. The at least one light source may include at least one white light LED.

BRIEF DESCRIPTION OF THE DRAWINGS

The accompanying drawings illustrate a number of exemplary embodiments and are part of the specification. Together with the following description these drawings demonstrate and explain various principles of the instant disclosure.

DETAILED DESCRIPTION

The light-emitting devices presented in the instant disclosure may include features optimized for helping a user detect a red color, and particularly a blood red color. According to various embodiments, light-emitting devices may have light sources that output a spectrum optimized for helping a user detect blood. In other words, a light-emitting device may be configured to output a light spectrum that is optimized to the reflective properties of blood. A light-emitting device may also be configured to output a light spectrum optimized to cause a human's vision system to respond to blood red colors such that the human perceives the blood red colors as standing out in contrast to other colors, including low wavelength non-blood red colors. Light-emitting devices discussed herein may also provide various other features and advantages.

The output of light may result from a subtractive method as compared to the additive methods described above. The subtractive methods may involve use of at least one filter (e.g., filter member or filter material). The filter may include an absorptive material that may pass certain wavelengths or attenuate certain wavelengths of visible light through absorption or reflection. The filters may be configured as notch filters or short-pass filters. The filter may be used with various types of light sources (e.g., bulb, LED or lantern) and various light source colors (e.g., green, blue, red or white). The filter may be particularly useful with white light sources, which typically provide maximum light intensity.

The filter may provide progressive attenuation of visible light wavelengths up to a blood red color wavelength, and pass light wavelengths for blood red color and higher wavelengths. In one example, the filter passes wavelengths for most blue and green colors, provides increasing attenuation through yellow and orange colors, provides maximum attenuation for red colors with wavelengths less then blood red color, and passes wavelengths for blood red color and higher wavelength colors. The wavelength of blood red color is typically in the range of about 610 nm to about 618 nm, and particularly about 614 nm, which may be referred to as a critical or threshold wavelength for attenuation using the filter. In at least some examples, the filter may provide progressive attenuation of light in the yellow, orange and red wavelengths up to the critical or threshold wavelength, and then pass wavelengths at or greater than the critical or threshold wavelength.

Figure 4:
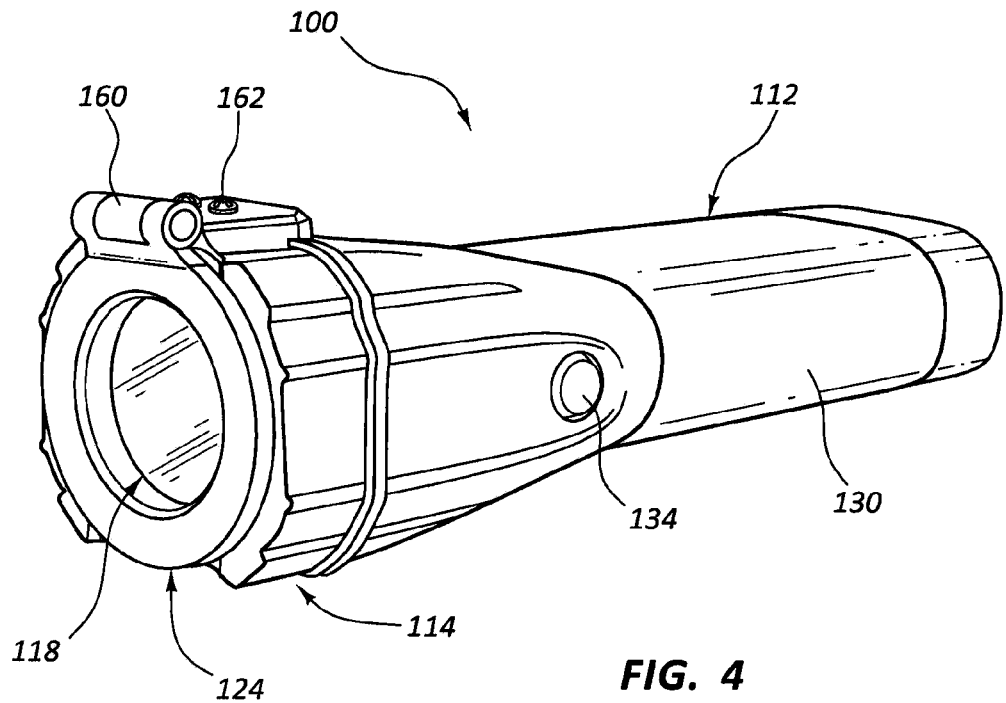
FIG. 4 is a perspective view of another example light emitting device in accordance with the present disclosure.
Figure 5:
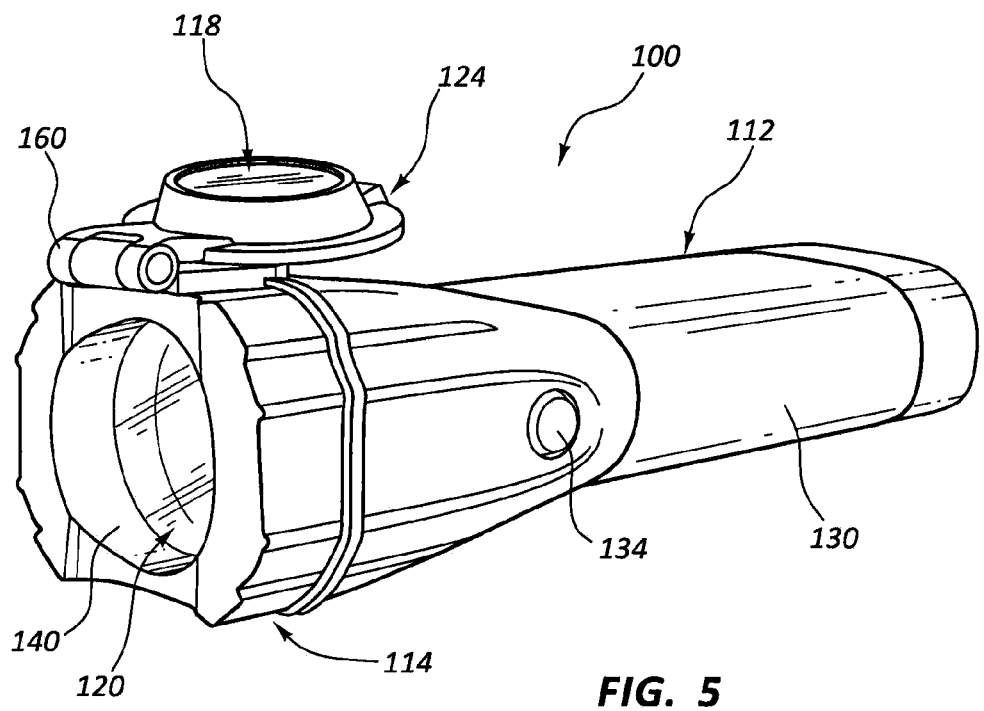
FIG. 5 is a perspective view of the light emitting device of FIG. 4 with a filter of the device adjusted into an inoperative position.
Figure 6:
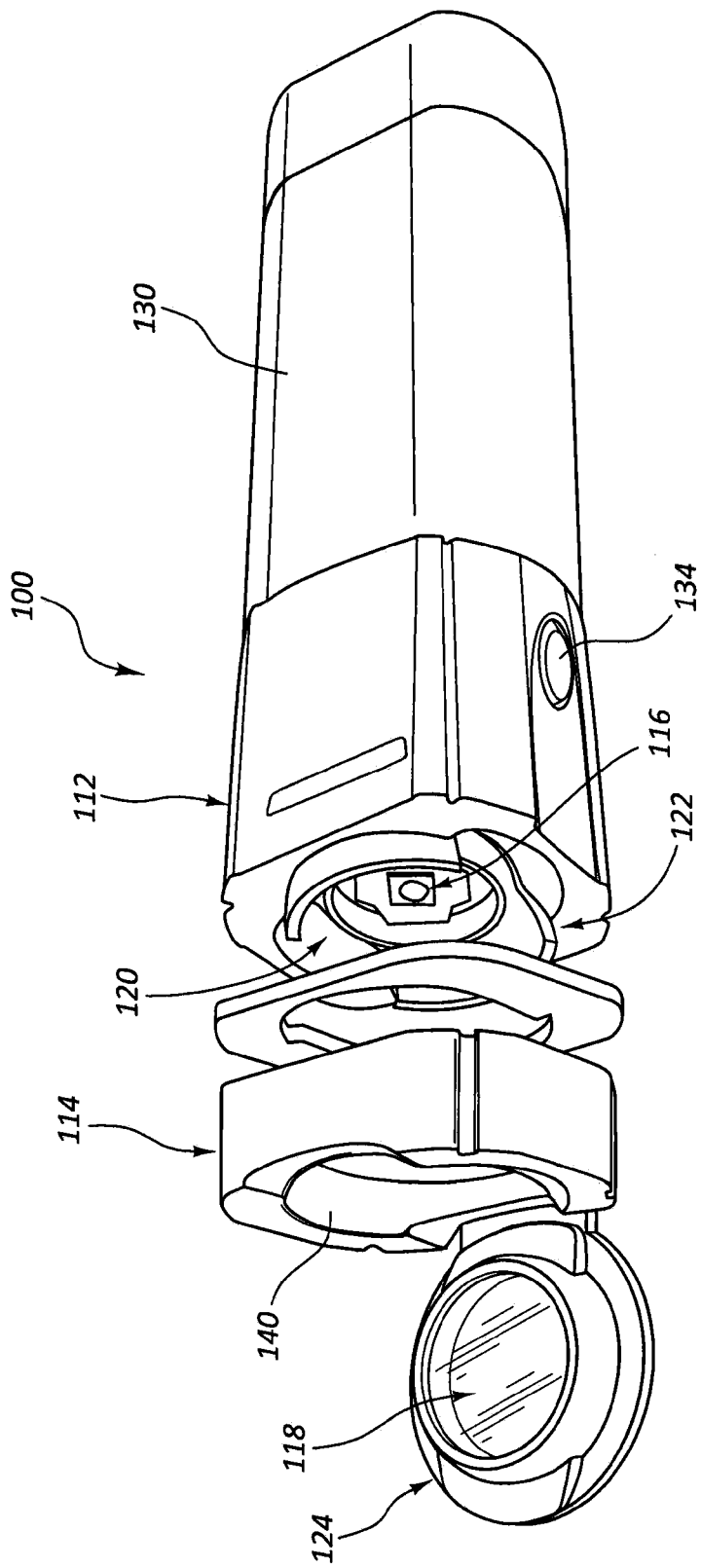
FIG. 6 is an exploded perspective view of the light emitting device of FIG. 4.

Light-emitting devices optimized to detect a blood red color may be implemented in various configurations. For example, the embodiment illustrated with respect to FIGS. 1-3 has a fixed filter that provides constant filtering when the light-emitting device is turned on. The embodiment illustrated in FIGS. 4-6 provides an adjustable filter, wherein the light-emitting device may be used in a filtering mode or an unfiltered mode depending on the adjusted position of the filter.

Figure 1:
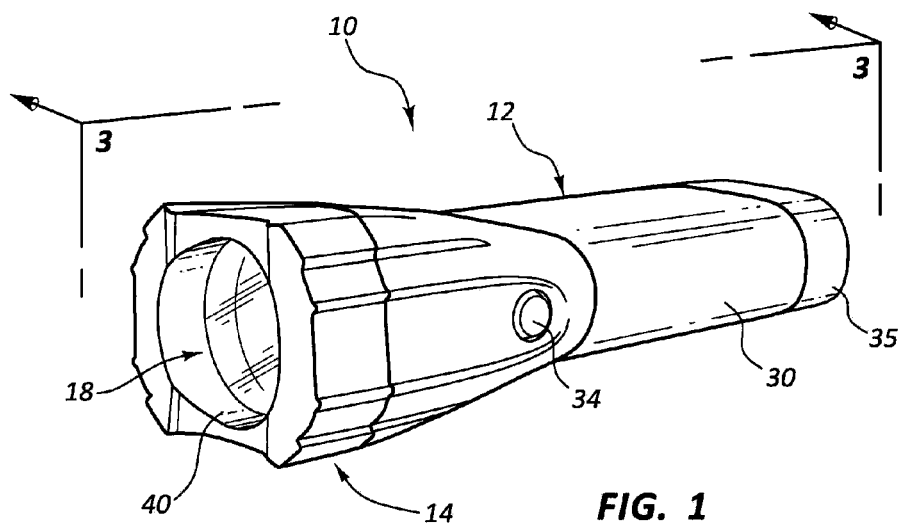
FIG. 1 is a perspective view of an example light emitting device in accordance with the present disclosure.
Figure 2:
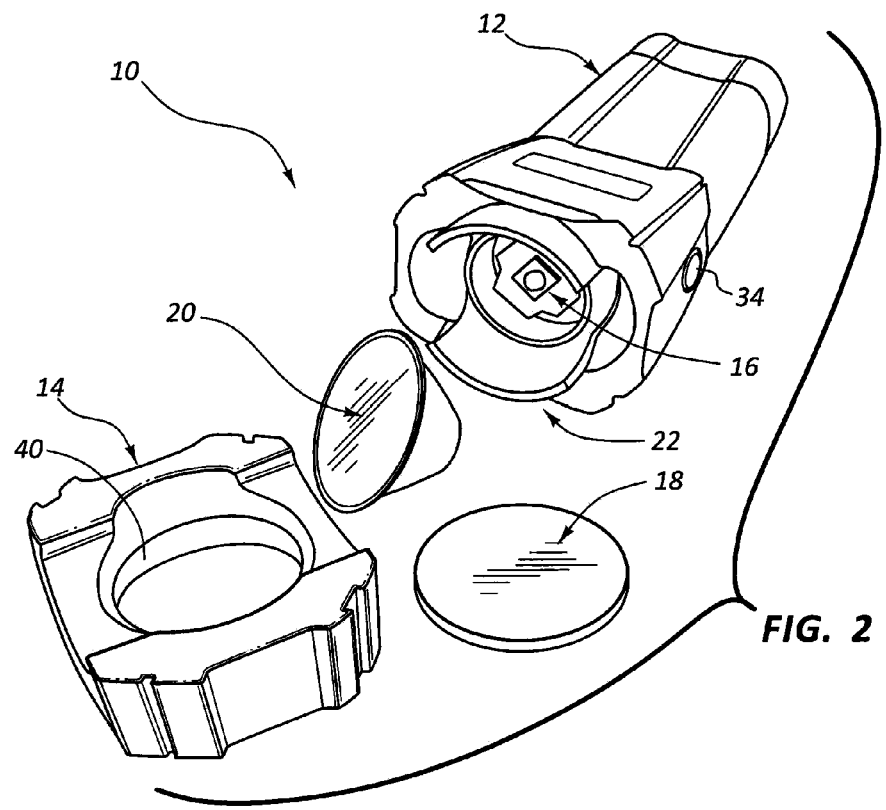
FIG. 2 is an exploded perspective view of the light emitting device of FIG. 1.
Figure 3:
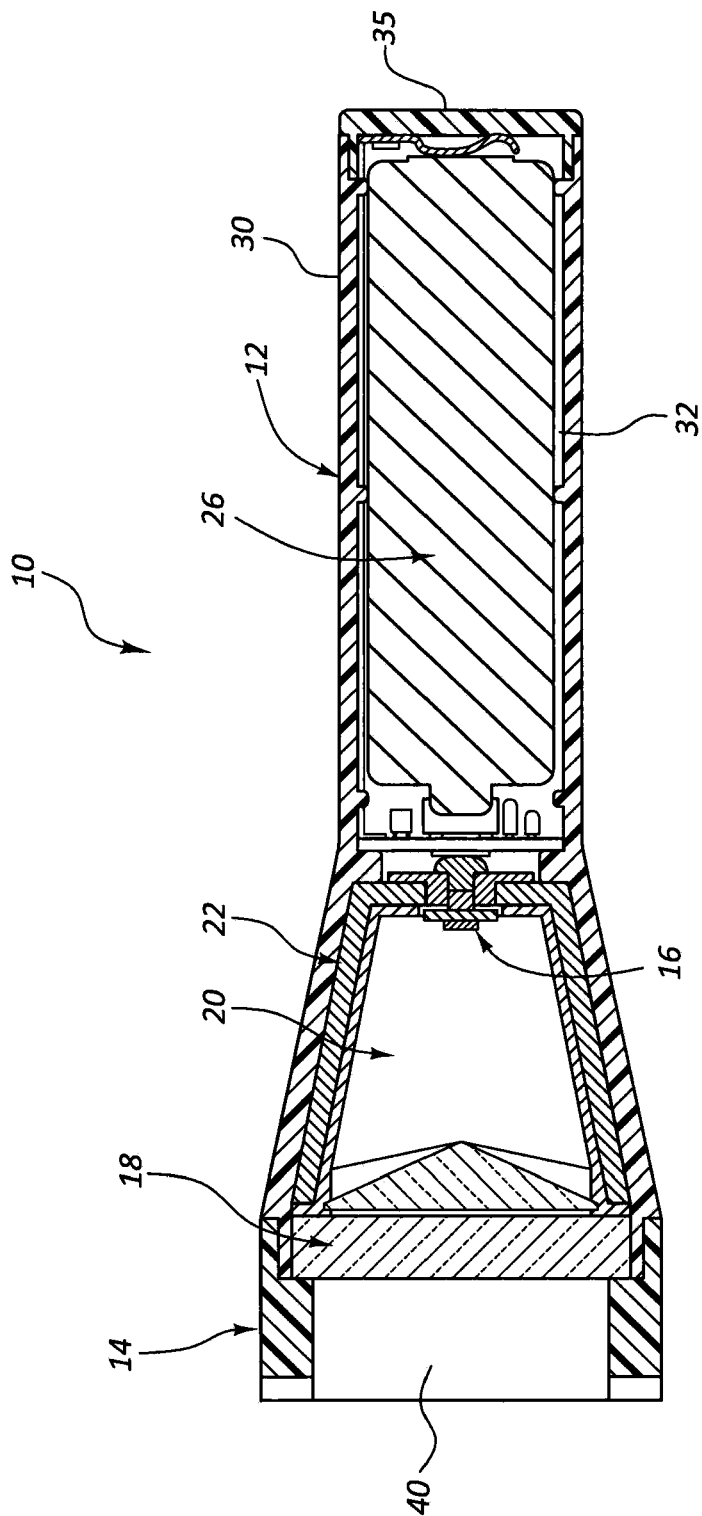
FIG. 3 is a cross-sectional view of the light emitting device of FIG. 1 taken along cross-section indicators 3-3.

FIGS. 1-3 illustrate a light emitting device 10. The light emitting device 10 includes a housing 12, a cap 14, a light source 16, a filter 18, a lens 20, a lens holder 22, and batteries 26, as shown in the cross-sectional view of FIG. 3. The cap 14 is removably mounted to housing 12. The light source 16, filter 18, lens 20 and lens holder 22 may be accessible by removing cap 14 from housing 12. The batteries 26 may be accessible upon removal of an end cover 35, which is positioned at an opposite end of housing 12 from cap 14. Light source 16 may comprise any desired light source including, for example, a light emitting diode (LED) or bulb (e.g., incandescent, zenon or halogen bulb). The light source may generate any desired color of light including, for example, white light, blue light, green light or red light. Light source 16 may comprise multiple light members that each generates a separate color of light. For example, light source 16 may include separate light bulbs that generate white, red, and green light. Light emitting device 10 may be adjustable to turn on one of the light members at a time for different color modes. In other examples, light source 16 may include a plurality of light members that each generates the same color of light and may be individually controlled.

Filter 18 is typically positioned at an outlet site of lens 20. Light from light source 16 passes through lens 20 and filter 18 and then out of cap 14. In arrangements in which the light emitting device 10 includes a reflector in place of or in addition to lens 20, light emitted from light source 16 may pass through and/or reflect off from a surface of the reflector before passing through filter 18. The lens 20 and/or reflector provides shaping of the light beam emitted by light source 16. Filter 18 may have any desired shape and size. In at least some examples, the shape and size (e.g., thickness) or other physical properties that filter 18 may affect its filtering properties. In one example, filter 18 has a disc-shaped construction. Further details concerning functionality of filter 18 are provided below.

Filter 18 is mounted to housing 12 by connecting cap 14 to housing 12. Filter 18 may maintain a fixed position relative to lens 20 and light source 16 during operation of light emitting device 10. Light emitting device 10 may be referred to as a fixed or permanent filter device.

Lens 20 is shown in at least FIGS. 2 and 3 having a generally conical or truncated conical shape. Lens 20 is configured to focus or magnify light generated by light source 16 and direct the light in a forward direction out of an opening 40 in cap 14. The lens 20 may be held in a fixed position with lens holder 22. All of the light generated by light emitting device 10 typically passes through lens 20.

One option for reducing the complexity of the light emitting device 10 and other devices disclosed herein would be to combine the filter 18 and lens 20 in a single structure. The optical filter 18 and lens 20 may be formed as a single, integral piece, wherein the resultant filtering lens member provides the filtering functionality described herein.

Batteries 26 provide a power source for operating light source 16. Batteries 26 may be replaced with other types of power sources. In some arrangements, light emitting device 10 is powered remotely from housing 12.

Housing 12 includes a handle portion 30 and an interior 32 (see FIG. 3). Handle portion 30 may be sized for grasping by a user. An on/off switch 34 may be positioned at an approximate midpoint a long a length of housing 12. The on/off switch 34 may be positioned at other locations on housing 12 such as adjacent to cap 14. In some embodiments, a separate on/off switch may be integrated into the cover 35, which is positioned at an end of housing 12 at a location opposite cap 14. For example, the cover 35 may include a depressible portion that actuates an internal on/off switch.

Referring to FIGS. 4-6, another example light emitting device 100 is shown and described. Light emitting device 100 includes a housing 112, a cap 114, a light source 116, a filter 118, a lens 120, a lens holder 122, and a filter connector 124, as shown in at least FIG. 6. Light emitting device 100 may also include a power source such as the batteries 26 described above with reference to light emitting device 10. Light emitting device 100 may include an on/off switch 134 that provides control of the light source.

Light emitting device 100 may have the same or similar functionality as light emitting device 10 with exception of the adjustability of filter 118 via filter connector 124. Filter connector 124 may be connected to cap 114 with a hinge 160 and fasteners 162. Filter connector 124 provides adjustable positioning of filter 118 between an operation position shown in FIG. 4 and a removed or inoperable position shown in FIG. 5. In the operation position of FIG. 4, filter 118 filters light emitted from light emitting device 100. When in the inoperable position of FIG. 5, light emitted from light emitting device 100 is unaffected by filter 118.

The light emitting device 100 provides for filtering of the emitted light when the filter 118 is positioned within an opening 140 of cap 114 and within an optical path of a light beam projecting from the light emitting device 100. When the filter 118 is removed from the optical path by rotating the filter connector 124 into the inoperable position shown in FIG. 5, the emitted light beam is projected unfiltered. Typically, filter 118 provides enhanced detection of blood, but also reduces intensity of the light beam projecting from the light emitting device 100. Providing adjustability of the position of the filter 118 according to the embodiment of FIGS. 4-6 presents the user with a way to pass the entire light beam at its maximum intensity in one setting or mode, while in another mode provide optimum blood tracking by filtering the emitted light beam.

Figure 7:
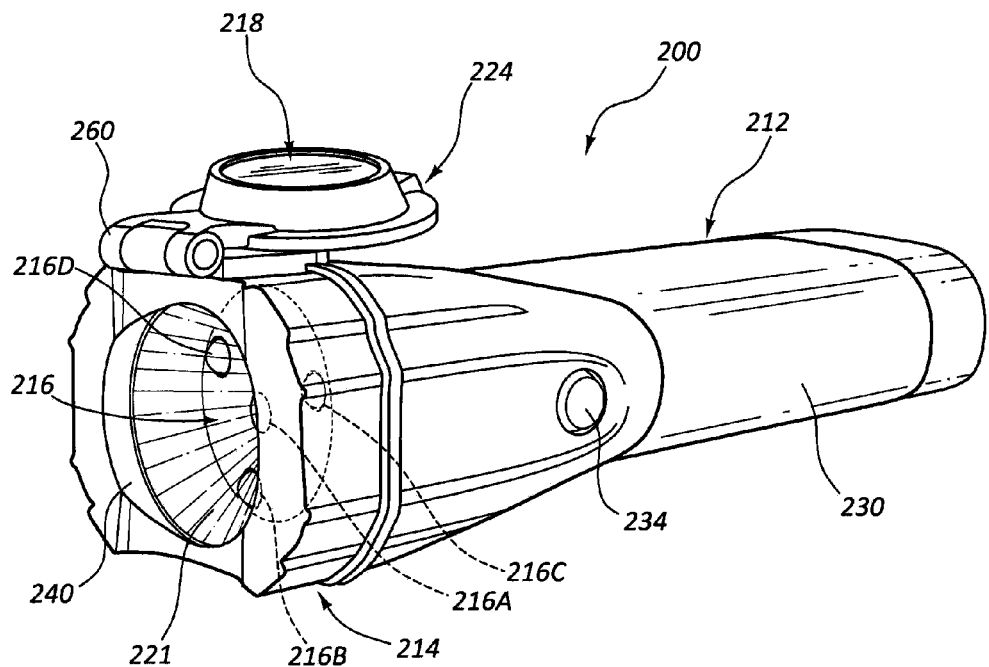
FIG. 7 is a perspective view of another example light emitting device in accordance with the present disclosure.
Figure 8:
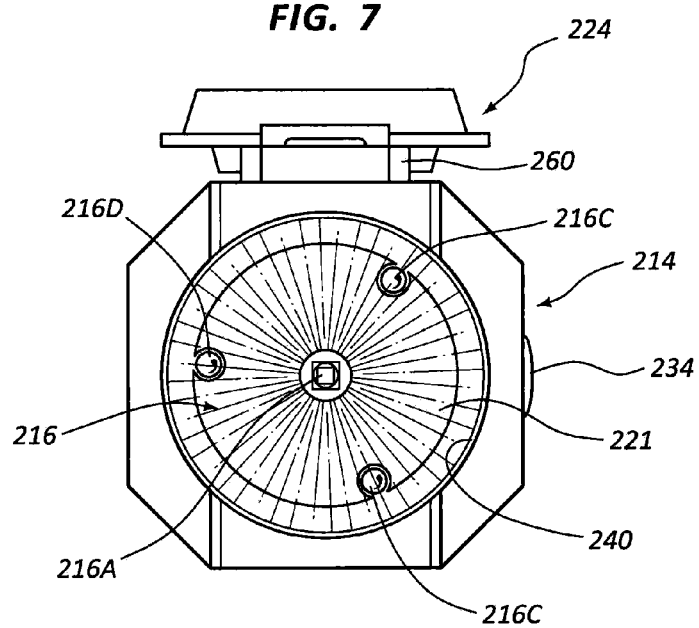
FIG. 8 is an end view of the light emitting device of FIG. 7.

Referring to FIGS. 7 and 8, another example light emitting device 200 is shown and described. Light emitting device 200 includes a housing 212, a cap 214, a light source 216, a filter 218, a reflector 221, and a filter connector 224, as shown in at least FIG. 7. Light emitting device 200 may also include a power source such as the batteries 26 described above with reference to light emitting device 10. Light emitting device 200 may include an on/off switch 234 that provides control of the light source 216 and may assist in operating light emitting device 200 in different modes. Generally, light emitting device 200 may be referred to as a multi-light, multi-mode device. Other light emitting devices that utilize a lens in addition to or in place of reflector 221 may also be configured as multi-light, multi-mode devices.

Light source 216 may include a plurality of light sources 216A-D. At least some of the light sources 216A-D (e.g., light sources 216B-D positioned around a periphery of and embedded in reflector 221—see FIG. 8) may be multi-color light sources, such as a plurality of LED packages that each includes green, blue and red LEDs. At least one of the light sources 216A-D (e.g., light source 216B positioned centrally on and embedded in reflector 221—see FIG. 8) may be a white light source, such as a white LED.

Light source 216 may be operable in a plurality of modes. In one mode, the light source 216A (e.g., white light) alone is turned on. In another mode, the light sources 216B-D may be turned on and project the same color of light (e.g., one of green, blue or red light) and the light source 216A is turned off. In a further mode, any one of the light sources 216A-D is turned on alone, or any combination of light sources 216A-D may be turned on.

The light emitting device 200 provides for filtering of the emitted light when the filter 218 is positioned in an optical path of a light beam projecting from the light emitting device 200. Typically, filter 218 provides enhanced detection of blood regardless of the color of light emitted from light emitting device 200. Providing a plurality of different light sources and/or light colors and various modes of operating the light sources may provide additional functionality for light emitting device 200. Light emitting device 200 may be operated in various modes to project different colors of light, project filtered light, and project unfiltered light. Some colors of light generated by light source 216 may pass through filter 218 without being attenuated because the range of wavelengths of the generated light is outside of the wavelengths being attenuated by filter 218. Further, filter 218 may be adjustable between operable filtering positions (e.g., see filter 118 in FIG. 5) and inoperable positions (e.g., see FIG. 8).

Figure 9A:
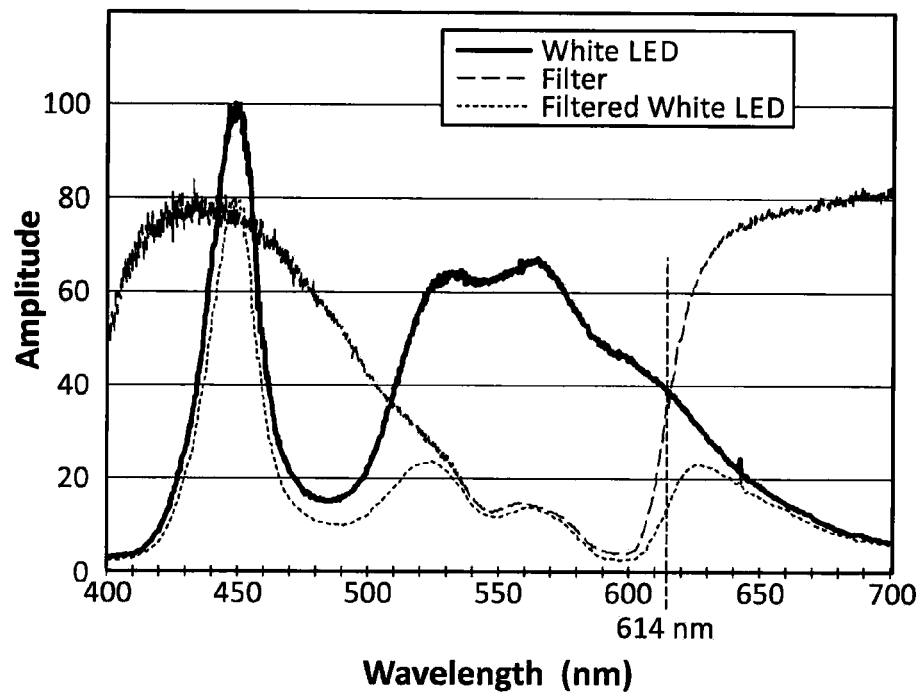
FIG. 9A is a graph showing a spectrum of a white light source, a spectral attenuation of an optical filter, and a spectrum of a resulting filtered light.
Figure 9B:
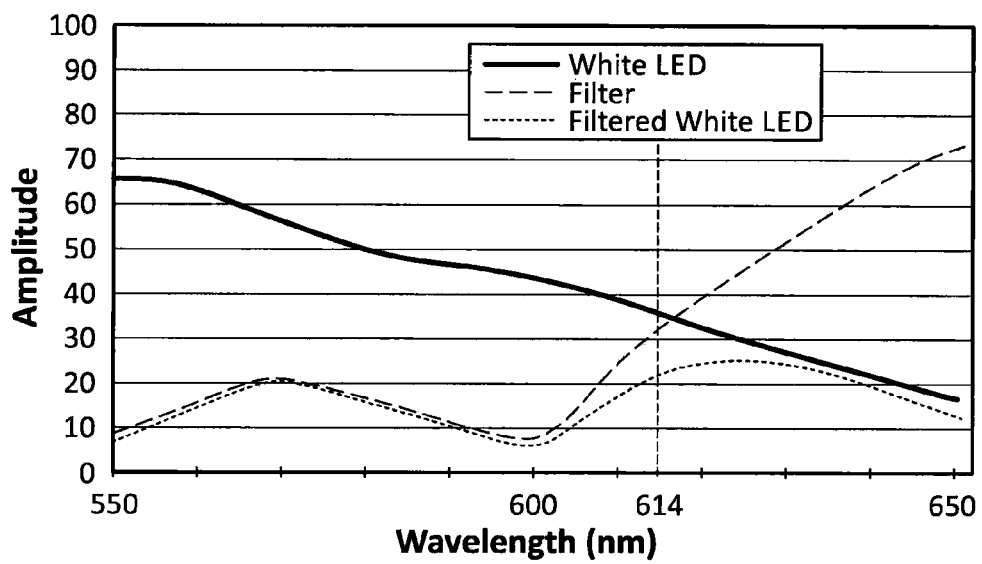
FIG. 9B is a close up view of a portion of the graph shown in FIG. 9A.

FIGS. 9A and 9B show the spectrum of three inputs: a white light source (white LED), an optical filter (e.g., an absorptive plastic filter), and the resultant filtered white light. FIG. 9A shows the visible light spectrum from 400 nm to 700 nm. FIG. 9B shows a narrow portion of the visible light spectrum from 550 nm to 650 nm. The plot of white light in FIG. 9A shows major blue components around 450 nm as well as green, yellow, orange and red components between 520 nm and 600 nm. The filter represented in FIG. 9A passes most blue light in the 400 nm to 500 nm range and progressively attenuates or blocks wavelengths from about 450 nm to about 600 nm. In the range of about 600 nm to about 620 nm the filter sharply changes to pass those wavelengths and higher wavelengths. Thus, the intensity of the resulting filtered white light is progressively attenuated in the green, yellow and orange color ranges up into the red light range for wavelengths less than blood red color. The intensity of the filtered white light is virtually zero in the red region between about 600 nm and about 610 nm. However, the intensity of the filtered light spectrum becomes quickly larger after about 610 nm in a transition wavelength where blood red colors exist so that blood red colors are passed. The transition wavelength is typically in the range of about 610 nm to about 618 nm, and more particularly about 614 nm. The 614 nm label shown in FIGS. 9A and 9B is representative of any transition wavelength within the range of about 610 nm to about 618 nm.

Figure 10A:
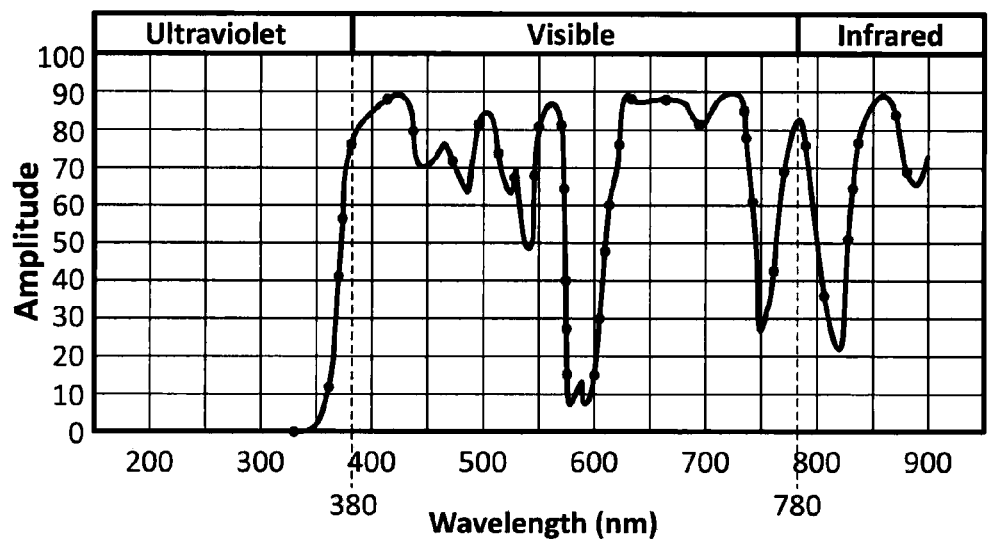
FIG. 10A shows a spectral response of a specialty glass containing Didymium.
Figure 10B:
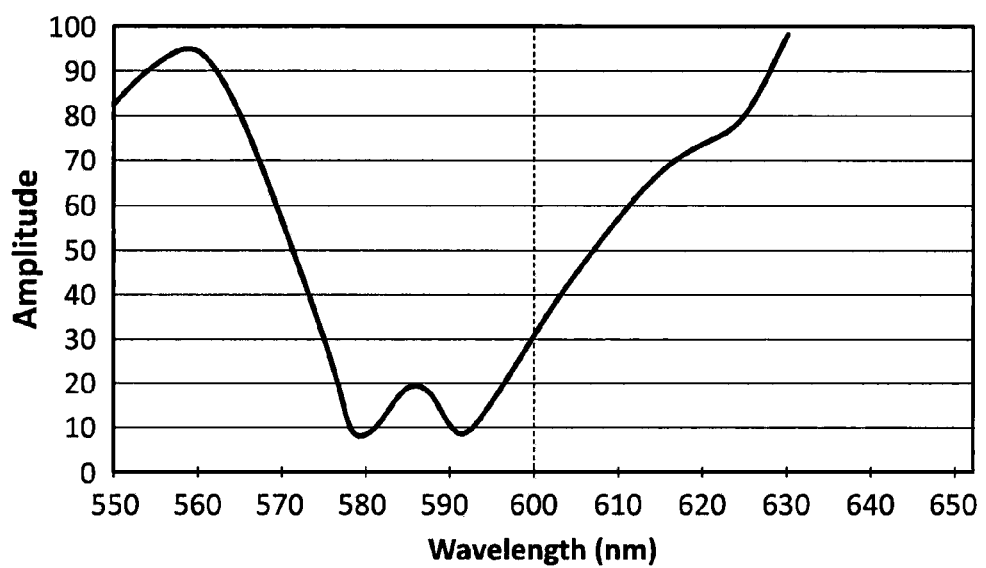
FIG. 10B is a close up view of a portion of the graph shown in FIG. 10A.

FIGS. 10A and 10B show the spectral response of a specialty glass containing didymium. The light is attenuated progressively in the wavelengths representing yellow and orange colors and low wavelength red colors, with the greatest attenuation in the low wavelength red colors that have wavelengths less than those of blood red colors. In the area of about 600 nm to about 620 nm the specialty glass passes the higher wavelength red colors thereby creating a sharp contrast in attenuated versus passed wavelengths through the red color band. FIG. 10B shows a limited portion of the spectrum from 550 nm to 650 nm showing the progressive attenuation below the transition or critical range of about 600 to about 620 nm.

Figure 11A:
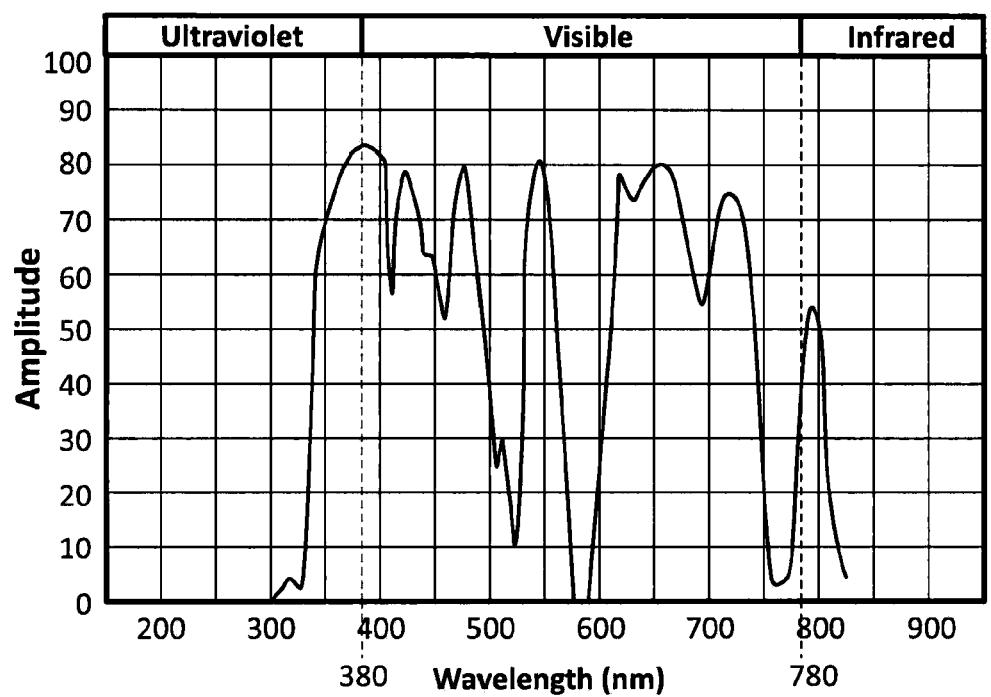
FIG. 11A shows a spectral response of a specialty amethyst contrast enhancement (ACE) glass.
Figure 11B:
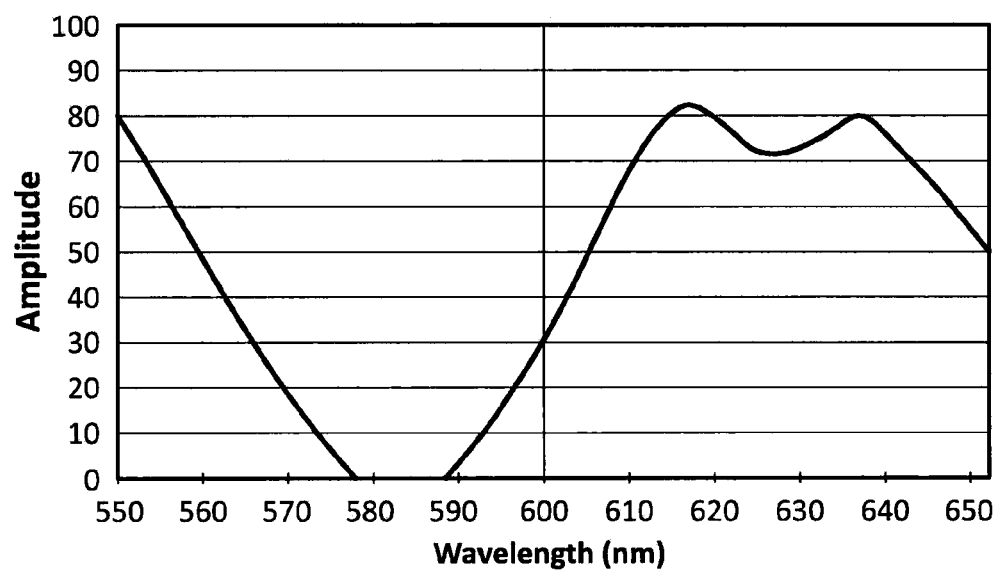
FIG. 11B is a close up view of a portion of the graph shown in FIG. 11A.

FIGS. 11A and 11B show a spectral response for a specialty amethyst contrast enhancement (ACE) glass. The wavelengths near about 600 nm (e.g., the critical transition wavelength) changes from heavy attenuation to a high pass of wavelengths. Wavelengths in the yellow, orange, and low wavelength red ranges are progressively attenuated while wavelengths are passed in the blood red color range and wavelengths greater than about 600 nm. FIG. 11B shows a limited portion of the spectrum from 550 nm to 650 nm showing a progressive attenuation leading up to blood red color and a sharp change at a transition wavelength between about 600 nm and about 620 nm, which includes the blood red color range.

Figure 12A:
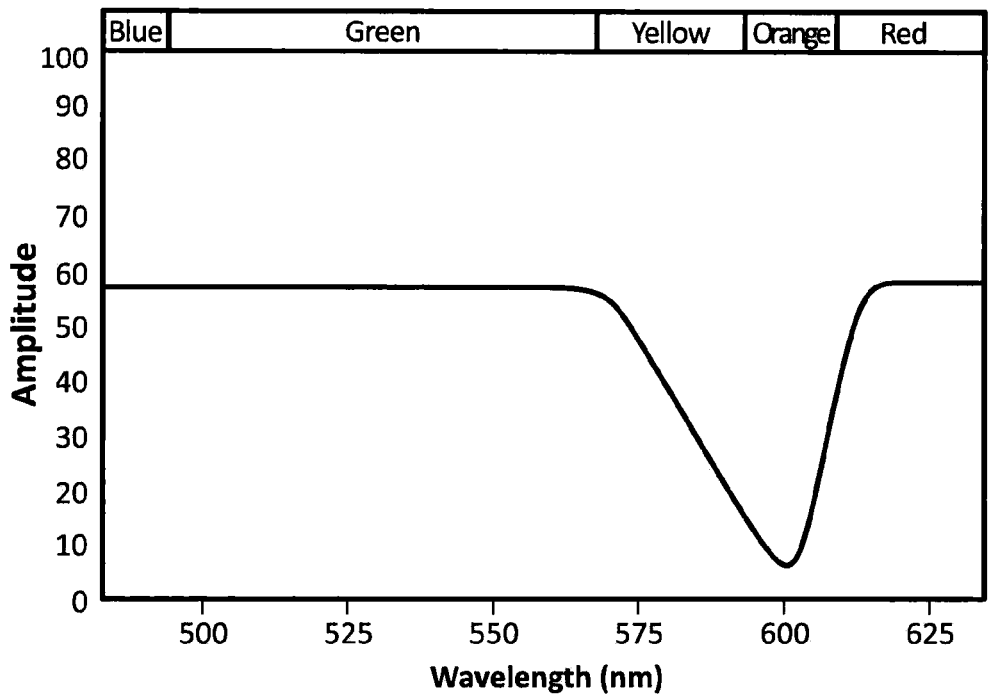
FIG. 12A shows a spectral response of an ideal optical filter in accordance with the present disclosure.
Figure 12B:
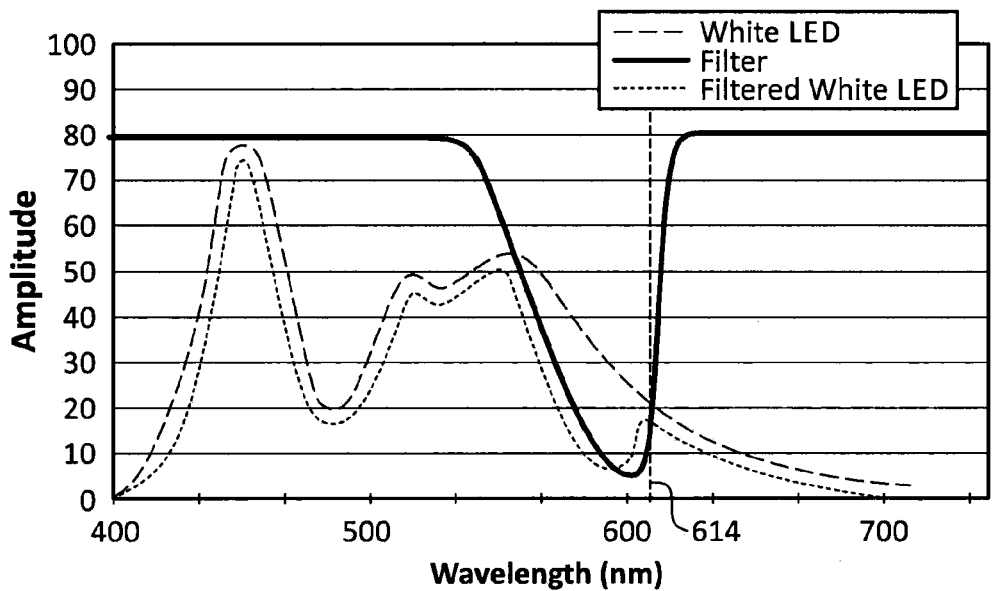
FIG. 12B is a graph showing a spectrum of a white light source, a spectral attenuation of the ideal optical filter shown in FIG. 12A, and a spectrum of a resulting filtered light.
Figure 12C:
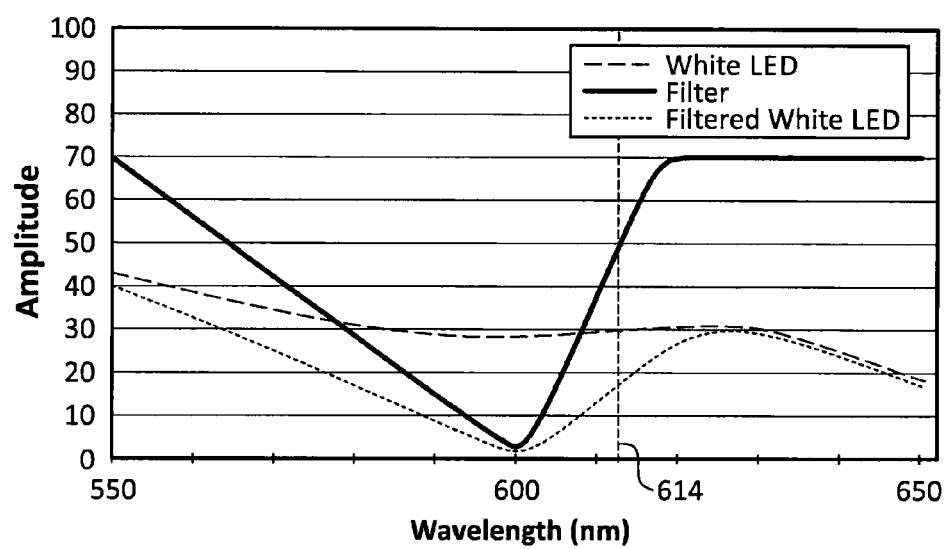
FIG. 12C is a close up view of a portion of the graph shown in FIG. 12B.

FIGS. 12A-12C show a spectral response for an ideal filter that maximizes the contrast between blood red colors and other colors, in particular colors having a wavelength in the orange and non-blood red color spectrum. The wavelengths leading up to about 600 nm to about 610 nm (e.g., the critical transition wavelength range) are progressively attenuated. A sharp transition to a high pass of wavelengths occurs at the critical transition wavelength. Wavelengths in the yellow, orange, and low wavelength red ranges are progressively attenuated while wavelengths are passed in the blood red color range and wavelengths greater than about 610 nm to about 618 nm. FIG. 12A shows a spectral response for the ideal filter. FIG. 12B shows the spectrum of three inputs: a white light source (white LED), an ideal filter, and the resultant filtered white light. FIG. 12C shows a narrow portion of the visible light spectrum from 550 nm to 650 nm from the graph of FIG. 12B. Ideally, the filter of FIG. 12A passes blue and green wavelengths, gradually attenuates through the yellow and orange wavelengths, has maximum attenuation in the blood red color wavelengths, and passes non-blood red wavelength greater than about 618 nm.

The graphs of FIGS. 9A-12C represent different materials that may be used for the filters 18, 118 described above with reference to FIGS. 1-6. The materials for the filter represented in FIGS. 9A and 9B may include a plastic such as a polycarbonate-based thermoplastic. Specialty narrow-band visible absorbing additives may be included in the thermoplastic to provide the desired filtering, wherein the filtering is a progressive attenuation leading up to and including colors having wavelengths less than blood red color and then passing wavelengths of blood red colors and colors having higher wavelengths. The filtering represented in FIGS. 9A and 9B may be described as heavily attenuating wavelengths directly adjacent to and less than the wavelengths of blood red colors and passing wavelengths of blood red colors and higher.

In another example (e.g., presented in FIGS. 10A and 10B), the combination of a rare earth mineral such as didymium with glass provides significant attenuation of yellow and orange colors and low wavelength red colors. Using the combined didymium and glass product with a high intensity white LED provides virtually no significant attenuation of blood red colors while significantly attenuating orange and low wavelength red colors. The product using didymium may be referred to as an interference filter wherein special interference filters are applied to glass, and the filters block wavelengths between green and red (e.g., notching out portions of yellow, orange and red colors).

In a further example (e.g., represented in FIGS. 11A and 11B), the use of amethyst contrast enhancement (ACE) with glass may involve custom interference patterns applied to glass, quarts, plastic or the like. Products including ACE may have similar attenuating functions as the product using didymium and the plastics with specialty narrowed-band visible absorbing additives described above with reference to FIGS. 9A-10B.

In all of the example materials and filters described herein, an upper critical wavelength may range from about 610 to about 618, and particularly about 614 nm, has been found to provide an optimized transition between heavy attenuation of a light and no attenuation of the light in order to maximize visualization of blood. This range of about 610 nm to about 618 nm typically coincides with blood red colors. This range may be expanded in some examples to include other wavelengths in the range of 600 nm to 620 nm. By filtering in a way in which any low wavelength non-blood red colors are most heavily attenuated, orange colors are significantly attenuated, yellow colors are attenuated less than the orange colors, and there is little or no attenuation of green colors (e.g., colors at a lower critical wavelength—e.g., in the range of about 550 nm and about 570 nm) and blue colors provides the best contrast to assist in illuminating blood.

Passing substantially all blue colors, most green colors, and at least some of the yellow and orange colors rather than completely blocking all of those colors may add more ambient light to the user's eye that assists in identifying and/or illuminating the blood red colors. Furthermore, passing blue, green and high wavelength red colors may make it possible to use the filters described herein (e.g., filters 18, 118) with flashlights that have multi-color capability. For example, a flashlight having the filter may include white, green, red and blue light sources (e.g., LEDs), and the individual colors may be powered sequentially to provide a red-only mode, a green-only mode, and a blue-only mode in addition to a white light blood-tracking mode.

A combination of the specialty plastic combined with a white light source, a rare mineral glass product combined with a white light source, or a specialty notch filter combined with a white light source may have particular advantages for illuminating blood red colors. The use of a white light source as opposed to color light sources may provide maximum light intensity even when filtered according to the methods disclosed herein. However, combining the filters described herein with other light sources such as red, green or blue light sources may still provide advantages as compared to other blood illumination products.

Further reiterating the principles described above, the present devices and methods may combine a high intensity light source (e.g., white light source) with special optical filters to produce an enhanced light spectrum optimized for the detection of blood red colors. The filtered light may represent an optimal light spectrum whereby contrast is enhanced so that blood red colors stand out against backgrounds comprising various colors in the visible light spectrum (e.g., red, orange, yellow, green, blue, etc.). The desired contrast is achieved not simply by completely blocking a range of wavelengths within the color spectrum, but instead employing a more sophisticated method of filtering to include progressive attenuation of colors based on their relative contrast to blood red colors. For example, an example device may pass (e.g., no significant attenuation) blue and green colors since these colors naturally contrast well against blood red colors. The device may at least partially attenuate yellow colors to increase contrast with blood red colors, more significantly attenuate orange colors more than the yellow color attenuation since orange colors are closer to blood red colors, and most significantly attenuate non-blood red colors to improve the contrast with nearby blood red colors.

The transition between the non-blood red colors and nearby blood red colors is of particular importance. A transition wavelength at which the progressive attenuation reaches its maximum attenuation, and after which there is no desire for any attenuation is typically in the range of about 600 nm to about 620 nm, particularly in the range of about 610 nm to about 618 nm, and more particularly about 614 nm. The wavelength of about 614 nm may be the optimal transition wavelength for may blood tracking applications. The transition wavelength of about 614 nm and nearby colors below this wavelength (e.g. about 580 nm to about 610 nm) are heavily attenuated, while nearby colors above this wavelength (e.g., 615 nm to about 640 nm) are not desired to have any attenuation. Setting the transition wavelength to a lower number (e.g., about 605 nm) may cause blood red colors to appear orange to an observer. Setting the color above 610 nm and below 618 nm typically causes blood red colors to appear red, or even bright red, to an observer.

The subtractive methods disclosed herein may enhance the detection of blood without producing any colored interference shadows. A custom optical filter may be used to progressively attenuate a white light source (or other colored light source) thereby attenuating (subtracting) portions of the white light's spectrum. The resulting light output typically does not exhibit any colored interference shadows. The progressive attenuation may provide additional contrast that is optimized to the optical properties of blood and to the responsivity of the human eye.

As discussed above, the physical implementation of the filters disclosed herein may include, but not be limited to: (1) optical interference patterns applied to glass, plastic and other substrates; (2) special absorptive pigments added to custom plastics; and (3) rare earth minerals mixed with glass or plastic such as didymium. These implementations may generally be referred to as subtractive methods, and are utilized in this application for the purpose of maximizing attenuation of wavelengths closest to blood red colors. Each of these implementations, when combined with high intensity white light sources, have produced significant contrast to help users identify blood red colors.

An alternative embodiment may implement a high intensity bulb (e.g., halogen, xenon, etc.) with a custom plastic filter, whereby the filter is specifically designed to progressively attenuate various colors based on their relative contrast to blood red colors. Further embodiments may use high intensity white LEDs with a custom optical filter created by a combination of, for example, rare earth minerals (e.g. didymium) and glass, whereby the resultant output light has a significant attenuation of yellow and orange colors and virtually no significant attenuation of blood red colors.

Blocking selective regions of an output spectrum of light from a light source may improve contrast. However, such selective blocking may significantly reduce the total output light intensity. This intensity reduction becomes more pronounced when wavelengths are blocked in the green portion of the spectrum where the human eye responsivity peaks. However, the total output intensity may be increased by using the progressive attenuation methods and devices described herein, whereby there is no desired attenuation of green or blue light. Blocking typically completely attenuates parts or portions of the output spectrum. In contrast, progressive attenuation only partially attenuates portions of the output spectrum.

Throughout the drawings, identical reference characters and descriptions indicate similar, but not necessarily identical, elements. While embodiments of the instant disclosure are susceptible to various modifications and alternative forms, specific embodiments have been shown by way of example in the drawings and will be described in detail herein. However, one of skill in the art will understand that embodiments of the instant disclosure are not intended to be limited to the particular forms disclosed herein. Rather, the instant disclosure covers all modifications, equivalents, and alternatives falling within the scope of embodiments defined by the appended claims.

The preceding description has been provided to enable others skilled in the art to best utilize various aspects of the exemplary embodiments described herein. This exemplary description is not intended to be exhaustive or to be limited to any precise form disclosed. Many modifications and variations are possible without departing from the spirit and scope of the instant disclosure. It is desired that the embodiments described herein be considered in all respects illustrative and not restrictive, and that reference be made to the appended claims and their equivalents for determining the scope of the instant disclosure. In addition, for ease of use, the words "including" and "having," as used in the specification and claims, are interchangeable with and have the same meaning as the word "comprising."

What is claimed is:

1. A light-emitting device configured to illuminate blood, the light-emitting device comprising:
   a white light source configured to emit white light;
   a filter configured to illuminate blood having a maximum attenuation band, the maximum attenuation band comprising a first wavelength, a maximum attenuation wavelength, and a transition wavelength, portions of white light having less attenuation at the first wavelength than at the maximum attenuation wavelength and the transition wavelength, portions of white light having maximum attenuation at about the maximum attenuation wavelength between the first wavelength and the transition wavelength, the maximum attenuation band progressively attenuating white light from the first wavelength to the transition wavelength, the transition wavelength being within a red light spectrum of the white light, the first wavelength being within a range of about 450 nm to about 580 nm, the transition wavelength being within a range of about 610 nm to about 618 nm.

2. The light-emitting device of claim 1, wherein the transition wavelength is about 614 nm.

3. The light-emitting device of claim 1, wherein portions of the white light closest to and below the transition wavelength are the most attenuated by the filter.

4. The light-emitting device of claim 1, wherein portions of the white light above the transition wavelength are unattenuated.

5. The light-emitting device of claim 1, wherein yellow portions of the white light are at least partially attenuated, orange portions of the white light are more attenuated than the yellow portions, and red portions of the white light having a non-blood red color are more attenuated than the orange portions.

6. The light-emitting device of claim 1, wherein the filter is adjustable between an operable position in which the white light is filtered, and an inoperable position in which the white light is not filtered.

7. The light-emitting device of claim 1, further comprising at least one of an optical lens and a reflector positioned between the white light source and the filter.

8. A light-emitting device configured to illuminate blood, the light-emitting device comprising:
a flashlight housing;
a white light source mounted to the flashlight housing and configured to emit white light;
a filter configured to illuminate blood and mounted to the flashlight housing, the filter comprising an attenuated band and an non-attenuated band, the attenuated band providing greater attenuation of portions of white light than the non-attenuated band, the attenuated band having an upper end comprising a transition wavelength;
at least one of an optical lens and a reflector mounted to the flashlight housing between the white light source and the filter;
wherein the filter progressively and gradually attenuates portions of the white light within the attenuated band up to the transition wavelength in a range of about 610 nm to about 618 nm, the transition wavelength being at least partially attenuated.

9. The light-emitting device of claim 8, wherein the filter passes all portions of the white light having wavelengths greater than about 618 nm.

10. The light-emitting device of claim 8, wherein the filter attenuates all portions of the white light less than about 618 nm.

11. The light-emitting device of claim 8, wherein the filter attenuates non-blood red color portions of the white light having wavelengths less than about 618 nm to a greater extent than the attenuation of the yellow and orange portions of the white light.

12. The light-emitting device of claim 8, wherein the filter attenuates portions of the white light between an upper critical wavelength and a lower critical wavelength.

13. The light-emitting device of claim 12, wherein the upper critical wavelength is in the range of about 610 nm to about 618 nm, and the lower critical wavelength is in the range of about 550 nm and about 570 nm.

14. The light-emitting device of claim 8, wherein the filter includes glass mixed with at least one rare earth mineral, or includes amethyst contrast enhancement (ACE) glass.

15. The light-emitting device of claim 14, wherein the at least one rare earth mineral includes Didymium.

16. The light-emitting device of claim 8, wherein the filter includes interference patterns applied to at least one of glass, quartz and plastic.

17. The light-emitting device of claim 8, wherein the filter and the optical lens are formed as a single, monolithic structure.

18. A method of illuminating blood, comprising:
providing a light-emitting device having a white light source and a filter;
generating white light with the white light source;
progressively attenuating with the filter portions of the white light within a maximum attenuation band of the filter to form a filtered light beam, the maximum attenuation band attenuating portions of white light in the maximum attenuation band up to an upper wavelength, the upper wavelength being at an upper end of the maximum attenuation band, the upper wavelength being at least partially attenuated and within a range of about 610 nm to about 618 nm;
emitting the filtered light beam from the light-emitting device to illuminate a target location, causing a blood red color in the target location to be perceived as standing out in contrast to non-blood red colors.

19. The method of claim 18, wherein attenuating with the filter portions of the white light includes attenuating all portions of the white light up to and including non-blood red colors having a wavelength less than the range of about 610 nm to about 618 nm.

20. The method of claim 18, wherein attenuating with the filter portions of the white light includes passing all portions of the white light having wavelengths greater than the range of about 610 nm to about 618 nm.

21. The method of claim 18, wherein attenuating with the filter portions of the white light includes progressively attenuating lower wavelength portions of the white light approaching the range of about 610 nm to about 618 nm.

22. The method of claim 18, wherein attenuating portions of the white light includes progressively attenuating wavelengths from about 550 nm up to about 610 nm.

23. A light-emitting device configured to illuminate blood, the light-emitting device comprising:
a flashlight housing;
at least one light source mounted to the flashlight housing and configured to emit a plurality of different colors using a plurality of different light modes;
a filter configured to illuminate blood and mounted to the flashlight housing;
a reflector mounted to the flashlight housing between the at least one light source and the filter;
wherein the filter at least partially attenuates yellow portions of the white light having wavelengths of 450 nm or greater, orange portions of the white light are more attenuated than the yellow portions, and red portions of the white light having a non-blood red color are more attenuated than the orange portions, up to a wavelength in the range of about 610 nm to about 618 nm.

24. The light-emitting device of claim 23, wherein the filter passes all portions of the light having wavelengths greater than about 618 nm.

25. The light-emitting device of claim 23, wherein the at least one light source includes a plurality of multi-color LEDs.

26. The light-emitting device of claim 25, wherein the at least one light source includes at least one white light LED.

* * * * *